United States Patent [19]

Schmidt et al.

[11] Patent Number: 4,528,136

[45] Date of Patent: Jul. 9, 1985

[54] PROCESS FOR PREPARING 2-[BIS(ARYL)METHYL]BENZOIC ACIDS

[75] Inventors: Paul J. Schmidt, Sharonville, Ohio; Patrick J. Jefferies, Fort Mitchell, Ky.

[73] Assignee: The Hilton-Davis Chemical Co., Cincinnati, Ohio

[21] Appl. No.: 484,831

[22] Filed: Apr. 14, 1983

Related U.S. Application Data

[62] Division of Ser. No. 328,918, Dec. 9, 1981, Pat. No. 4,399,291.

[51] Int. Cl.$^3$ .............................................. C09B 11/10
[52] U.S. Cl. .................................. 260/391; 260/393
[58] Field of Search ................................ 260/393, 391

[56] References Cited

U.S. PATENT DOCUMENTS

| | | | |
|---|---|---|---|
| Re. 23,024 | 8/1948 | Adams | 260/344.6 |
| 2,417,897 | 3/1947 | Adams | 260/344.6 |
| 3,739,000 | 6/1973 | Lodolini et al. | 260/393 |
| 3,971,821 | 7/1976 | Baumann | 260/465 E |
| 3,995,088 | 11/1976 | Garner et al. | 428/323 |
| 4,045,458 | 8/1977 | Kondo et al. | 260/393 |
| 4,330,476 | 5/1982 | Hermann | 260/393 |
| 4,455,435 | 6/1984 | Dundon et al. | 260/391 |

FOREIGN PATENT DOCUMENTS 2072163  9/1981  United Kingdom ............... 260/393

OTHER PUBLICATIONS

*The Chemistry of Synthetic Dyes*, Venkataraman, vol. II, pp. 711–713, 1952, Academic Press Inc., New York, N.Y.

Beilsteins Handbuch der Organische Chemie, vol. 14, p. 549.

*Primary Examiner*—Glennon H. Hollrah
*Assistant Examiner*—Raymond Covington
*Attorney, Agent, or Firm*—Terrence E. Miesle; Paul E. Dupont; B. Woodrow Wyatt

[57] ABSTRACT

Process comprises the combination of the two steps of condensing Y-benzaldehyde with N-$R^2$-N-$R^3$-aniline and 3-N-R-N-$R^1$-benzoic acid, under acidic conditions to produce 2-[(Y-phenyl) (4-N-$R^2$-N-$R^3$-aminophenyl)-methyl]-5-N-R-N-$R^1$-aminobenzoic acid, and oxidizing said benzoic acid to produce 3-(Y-phenyl)-3-(4-N-$R^2$-N-$R^3$-aminophenyl)-6-N-R-N-$R^1$-aminophthalide.

5 Claims, No Drawings

PROCESS FOR PREPARING 2-[BIS(ARYL)METHYL]BENZOIC ACIDS

CROSS REFERENCE TO RELATED APPLICATIONS

This application is a division of application Ser. No. 328,918, filed Dec. 9, 1981, now U.S. Pat. No. 4,399,291.

BACKGROUND OF THE INVENTION (a) Field of the Invention

This invention relates to a novel two-step process for the preparation of 3,3-bis(phenyl)phthalides useful in the art of carbonless duplicating as, for example, in pressure-sensitive systems and in thermal marking systems and to a novel process for the preparation of 2-[bis(phenyl)methyl]benzoic acid intermediates to said phthalides.

(b) Description of the Prior Art

It is well established in the dyestuff art that benzaldehyde condenses with two equivalents of aniline in the presence of an acidic material, for example, sulfuric acid to form diaminotriphenylmethane. Similarly, the condensation of p-aminobenzaldehyde with two equivalents of aniline yields leuco Pararosaniline, 4,4',4''-triaminophenylmethane. And in an analgous reaction leuco crystal violet, 4,4',4''-tris(dimethylaminophenyl)methane is obtained from the interaction of p-dimethylaminobenzaldehyde with two equivalents of N,N-dimethylaniline in the presence of an acidic material. On the other hand, the chemical moiety known as 3,3-bis(4-dimethylaminophenyl)-6-dimethylaminophthalide, commonly known as Crystal Violet Lactone or simply CVL is prepared by a number of synthetic routes. One such route is the multi-step synthesis in which Michler's hydrol, 4,4'-dimethylaminobenzhydrol, is reacted with 3-dimethylaminobenzoic acid in the presence of sulfuric acid to obtain 2-[bis(4-dimethylaminophenyl)methyl]-5-dimethylaminobenzoic acid which is isolated. Then said isolated benzoic acid is oxidized in a second step to obtain the phthalide known as CVL. However, the Michler's hydrol used as an intermediate in the process for preparing CVL is itself, prepared by a two-step synthesis. In the first step, two equivalents of N,N-dimethylaniline and formaldehyde are interacted to obtain Michler's methane which is isolated. In the second step, Michler's methane is oxidized with lead dioxide to obtain Michler's hydrol.

In a second synthetic route to CVL, which is also a multi-step synthesis, 4-dimethylaminobenzaldehyde is reacted with 3-dimethylaminobenzoic acid to obtain 3-(4-dimethylaminophenyl)-6-dimethylaminophthalide in the first step. In a second step, the 3-(4-dimethylaminophenyl)-6-dimethylaminophthalide from step one is interacted with N,N-dimethylaniline in the presence of a Friedel-Crafts type catalyst to obtain 2-[bis(4-dimethylaminophenyl)methyl]-5-dimethylaminobenzoic acid. In a third step, the benzoic acid from step two is oxidized to obtain 3,3-bis(4-dimethylaminophenyl)-6-dimethylaminophthalide.

In another known process for the preparation of CVL there are three steps. The first step comprises the interaction of the methyl ester of 2-formyl-5-dimethylaminobenzoic acid with two equivalents of N,N-dimethylaniline to obtain the methyl ester of 2-[bis(4-dimethylaminophenyl)methyl]-5-dimethylaminobenzoic acid. After isolation, this benzoic acid is oxidized in the second step and finally in the third step the oxidized product is saponified and the lactone ring is closed to obtain the 3,3-bis(4-dimethylaminophenyl)-6-dimethylaminophthalide (CVL).

In all of these art-known processes there are a multiple of synthetic steps required usually with isolation of the intermediate material after each of the steps. In addition, many of the starting materials required for these processes themselves have to be made by processes involving one or more synthetic steps. Each step required increases the cost of the final desired product, uses additional valued raw materials and increases the disposal problems of both the liquid and solid wastes from the overall synthetic processes.

The following items to date appear to constitute the most relevant prior art with regard to the instant invention.

U.S. Pat. No. 2,417,897 and its corresponding U.S. Pat. No. Re. 23,024, which issued Mar. 25, 1947 and Aug. 17, 1948, respectively, disclose a three-step process for the preparation of 3,3-bis(4-dimethylaminophenyl)-6-dimethylaminophthalide, Crystal Violet Lactone (CVL). In the first step, 3-dimethylaminobenzoic acid is prepared from 3-aminobenzoic acid by alkylating the free amine using methyl iodide in the presence of potassium hydroxide. In the second step, the 3-dimethylaminobenzoic acid is condensed with 4,4'-bis(dimethylamino)benzhydrol in the presence of sulfuric acid to obtain 2-[bis(4-dimethylaminophenyl)methyl]-5-dimethylaminobenzoic acid. In the third step, the 2-[bis(4-dimethylaminophenyl)methyl]-5-dimethylaminobenzoic acid is oxidized using lead dioxide in dilute hydrochloric acid to obtain the CVL.

U.S. Pat. No. 4,045,458, which issued Aug. 30, 1977 discloses a process for the preparation of 2-[bis(4-dialkylaminophenyl)methyl]-5-dialkylaminobenzoic acids by condensing a 3-(4-dialkylaminophenyl)-6-dialkylaminophthalide with an N,N-dialkylaniline in the presence of a Friedel-Crafts type catalyst. The patent further discloses a process in which the 2-[bis(4-dialkylaminophenyl)methyl]-5-dialkylaminobenzoic acid obtained in the above process can be oxidized utilizing various oxidizing agents to obtain 3,3-bis(4-dialkylaminophenyl)-6-dialkylaminophthalides.

In the fourth Edition of Beilsteins Handbuch der Organische Chemie, Vol. 14, page 549, 4,4''-bis-dimethylaminotriphenylmethanecarbonsaure-(2) is reported as a by-product in the preparation of 3-(4-dimethylaminophenyl)phthalide by the condensation of dimethylaniline with o-phthalaldehydic acid in the presence of a catalyst such as zinc chloride, phosphorous oxychloride or potassium bisulfate.

U.S. Pat. No. 3,971,821, issued July 27, 1976, discloses a three-step process for the preparation of 3,3-bis(4-dimethylaminophenyl)-6-dimethylaminophthalide which comprises in the first step reacting the methyl ester of 2-formyl-5-dimethylaminobenzoic acid with two molecular equivalents of N,N-dimethylaniline to obtain the methyl ester of 2-[bis(4-dimethylaminophenyl)methyl]-5-dimethylaminobenzoic acid which in turn is oxidized in a second step and the oxidized product is saponified in the third step to obtain the 3,3-bis(4-dimethylaminophenyl)-6-dimethylaminophthalide (CVL).

U.S. Pat. No. 3,995,088, issued Nov. 30, 1976, discloses a process for the preparation of leuco methylene dyestuffs which involves the reaction of two molecular equivalents of a substituted N,N-dialkylaniline with one molecular equivalent of a benzaldehyde in the presence of an acidic substance and optionally having urea present during the reaction.

(c) Patent Activities of Others

British Patent Publication No. 2,072,163, which was published Sept. 30, 1981, teaches a process for the preparation of 2-[bis(4-dimethylaminophenyl)methyl]-5-dimethylaminobenzoic acid by interacting 4-dimethylaminobenzaldehyde, urea and N,N-dimethylaniline in hydrochloric acid. The reaction mass is then made alkaline and the excess N,N-dimethylaniline is steam distilled from the mixture and after cooling 1,3-bis(4',4''-dimethylaminodiphenyl-methyl)urea is obtained. The urea derivative is then reacted with 3-dimethylaminobenzoic acid in dilute sulfuric acid and after rendering the reaction mixture alkaline, 2-[4,4'-bis(-dimethylamino)benzhydryl]-5-dimethylaminobenzoic acid (Leuco Crystal Violet Lactone) is isolated. This reference appeared subsequent to applicants' invention described herein and less than one year prior to the filing date of this application.

SUMMARY OF THE INVENTION

In one of its process aspects, the invention relates to a two-step process for producing 3,3-bis(phenyl)substituted-phthalides which comprises interacting in the first step an aniline, a benzaldehyde and a benzoic acid to obtain 2-[bis(phenyl)methyl]benzoic acids which are oxidized in the second step to obtain the corresponding phthalides.

In a second of its process aspects, the invention relates to a process for producing 2-[bis(phenyl)methyl]-benzoic acids which comprises interacting an aniline, a benzaldehyde and a benzoic acid to obtain said 2-[bis(-phenyl)methyl]-substituted benzoic acids.

DETAILED DESCRIPTION INCLUSIVE OF THE PREFERRED EMBODIMENTS

More specifically, this invention in one of its process aspects resides in the novel process for the preparation of 3-(Y-phenyl)-3-(4-N-$R^2$-N-$R^3$-aminophenyl)-6-N-R-N-$R^1$-aminophthalides, which are particularly useful as colorless precursors in the art of carbonless duplicating and thermal marking, and which are of the formula

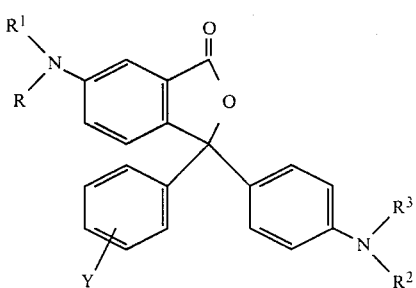

Formula I wherein R, $R^1$, $R^2$ and $R^3$ may be identical or different and each represents hydrogen, non-tertiary alkyl of one to four carbon atoms, hydroxyalkyl of two or three carbon atoms, phenyl, benzyl or phenyl or benzyl substituted in the benzene ring by one or two of halo or alkyl of one to three carbon atoms; and Y represents hydrogen, halo, non-tertiary alkyl of one to four carbon atoms, non-tertiary alkoxy of one to four carbon atoms, or dialkylamino or N-alkylbenzylamino in which alkyl is non-tertiary alkyl of one to four carbon atoms and benzyl may be substituted in the benzene ring by one or two of halo or alkyl of one to three carbon atoms which comprises in a first step, reacting in approximately equimolecular proportions a Y-benzaldehyde, an N-$R^2$-N-$R^3$-aniline and a 3-(N-R-N-$R^1$)aminobenzoic acid in which R, $R^1$, $R^2$, $R^3$ and Y each have the same respective meanings given for Formula I, in an acidic medium to produce a 2-[(Y-phenyl)(4-N-$R^2$-N-$R^3$-aminophenyl)methyl]-5-N-R-N-$R^1$-aminobenzoic acid of the formula

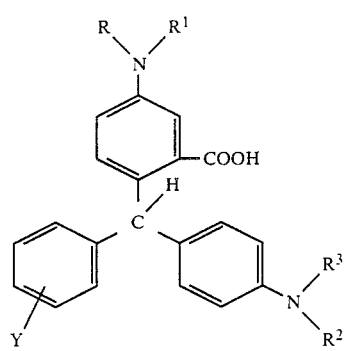

Formula II and in a second step, oxidizing said 2-[(Y-phenyl)(4-N-$R^2$-N-$R^3$-aminophenyl)methyl]-5-N-R-N-$R^1$-aminobenzoic acid of Formula II in an aqueous alkaline medium to produce a 3-(Y-phenyl)-3-(4-N-$R^2$-N-$R^3$-aminophenyl)-6-N-R-N-$R^1$-aminophthalide of Formula I.

In a first particular embodiment in accordance with its first process aspect, the invention sought to be patented resides in the novel process for preparing a 3-(4-Y-phenyl)-3-(4-N-$R^2$-N-$R^3$-aminophenyl)-6-N-R-N-$R^1$-aminophthalide of Formula I. Particularly preferred within this embodiment is the process for preparing a phthalide of Formula I wherein Y is dialkylamino or N-alkylbenzylamino in which alkyl is non-tertiary alkyl of one to four carbon atoms.

In a second particular embodiment in accordance with its first process aspect, the invention sought to be patented resides in the novel process for preparing a 3-(Y-phenyl)-3-(4-N-$R^2$-N-$R^3$-aminophenyl)-6-N-R-N-$R^1$-aminophthalide of Formula I wherein the acidic medium employed in the first step is selected from the group consisting of aqueous sulfuric acid, hydrochloric acid and methanesulfonic acid.

In a third particular embodiment in accordance with its first process aspect, the invention sought to be patented resides in the novel process for preparing a 3-(Y-phenyl)-3-(4-N-$R^2$-N-$R^3$-aminophenyl)-6-N-R-N-$R^1$-aminophthalide of Formula I wherein urea is present in the acidic medium of the first step.

This invention, in its second process aspect, resides in the process for preparing 2-[(Y-phenyl)(4-N-$R^2$-N-$R^3$-aminophenyl)methyl]-5-N-R-N-$R^1$-aminobenzoic acid of the formula

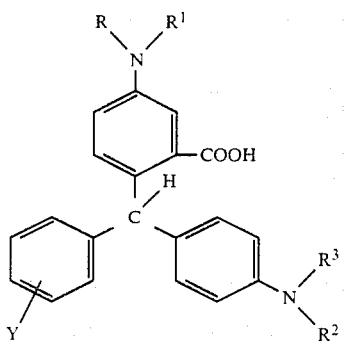

Formula II wherein R, $R^1$, $R^2$ and $R^3$ may be identical or different and each represents hydrogen, non-tertiary alkyl of one to four carbon atoms, hydroxyalkyl of two or three carbon atoms, phenyl or benzyl or phenyl or benzyl substituted in the benzene ring by one or two of halo or alkyl of one to three carbon atoms; and Y represents hydrogen, halo, non-tertiary alkyl of one to four carbon atoms, non-tertiary alkoxy of one to four carbon atoms, or dialkylamino or N-alkylbenzylamino in which alkyl is non-tertiary alkyl of one to four carbon atoms and benzyl may be substituted in the benzene ring by one or two of halo or alkyl of one to three carbon atoms which comprises reacting in approximately equimolecular proportions a Y-benzaldehyde, an $N-R^2-N-R^3$-aniline and a 3-N-R-N-$R^1$-aminobenzoic acid in which R, $R^1$, $R^2$, $R^3$ and Y each have the meanings given for Formula II, in an acidic medium.

In a first particular embodiment in accordance with its second process aspect, the invention sought to be patented resides in the novel process for preparing a 2-[(4-Y-phenyl)(4-N-$R^2$-N-$R^3$-aminophenyl)methyl]-5-N-R-N-$R^1$-aminobenzoic acid of Formula II. Particularly preferred within this embodiment is the process for preparing a 2-[(4-Y-phenyl)(4-N-$R^2$-N-$R^3$-aminophenyl)methyl]-5-N-R-N-$R^1$-aminobenzoic acid of Formula II wherein Y is a dialkylamino or N-alkylbenzylamino in which alkyl is a non-tertiary alkyl of one to four carbon atoms.

In a second particular embodiment in accordance with its second process aspect, the invention sought to be patented resides in the novel process for preparing a 2-[(Y-phenyl)(4-N-$R^2$-N-$R^3$-aminophenyl)methyl]-5-N-R-N-$R^1$-aminobenzoic acid of Formula II wherein the acidic medium is selected from the group consisting of aqueous sulfuric acid, hydrochloric acid and methanesulfonic acid.

In a third particular embodiment in accordance with its second process aspect, the invention sought to be patented resides in the novel process for preparing a 2-[(Y-phenyl)(4-N-$R^2$-N-$R^3$-aminophenyl)methyl]-5-N-R-N-$R^1$-aminobenzoic acid of Formula II wherein urea is present in the acidic medium.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also suitable for practicing the processes of this invention.

The term "dialkylamino in which alkyl is non-tertiary alkyl of one to four carbon atoms" denotes saturated, acyclic groups which may be straight or branched as exemplified by dimethylamino, diethylamino, ethylmethylamino, dipropylamino, dibutylamino, isobutylmethylamino and the like.

The term "N-alkylbenzylamino in which alkyl is non-tertiary alkyl of one to four carbon atoms and benzyl may be substituted in the benzene ring by one or two of halo or alkyl of one to three carbon atoms" denotes an amino moiety which is substituted with an acyclic group which may be straight or branched and one benzyl group as exemplified by N-methylbenzylamino, N-ethylbenzylamino, N-propylbenzylamino, N-sec-butylbenzylamino, N-ethyl(2,5-dimethylbenzyl)amino, N-ethyl(4-chlorobenzyl)amino and the like.

As used herein the terms "alkyl of one to three carbon atoms" and "non-tertiary alkyl of one to four carbon atoms" denote saturated monovalent straight or branched aliphatic hydrocarbon radicals including methyl, ethyl, propyl, isopropyl, butyl and isobutyl.

The term "non-tertiary alkoxy of one to four carbon atoms" include saturated acyclic, straight or branched-chained groups such as methoxy, ethoxy, propoxy, isopropoxy, butoxy, sec-butoxy and isobutoxy.

As used herein the term "hydroxyalkyl of two or three carbon atoms" denotes saturated monovalent straight or branched aliphatic hydrocarbon radicals containing a terminal hydroxy substituent including hydroxyethyl, hydroxypropyl, hydroxyisopropyl and the like.

As used herein the term "acidic medium" denotes any aqueous acidic medium capable of dispersing, partially dissolving or completely dissolving the reactants thus providing a fluid medium for these reactants to interact forming the desired 2-[bis(phenyl)methyl]benzoic acids. Examples of the acids which may be utilized in the aqueous acidic medium are sulfuric acid, hydrochloric acid, methanesulfonic acid, phosphorous acid, hydrobromic acid, acetic acid, chloroacetic acid, dichloroacetic acid and so forth.

The processes of this invention afford a novel convenient and economically advantageous synthetic route to a large number of known compounds which are 3,3-bis(phenyl)-6-N-R-N-$R^1$-aminophthalides of the type represented by Formula I. Many species defined by Formula I are well-known in the prior art as being useful as colorless precursors in carbonless duplicating systems, for example, 3,3-bis(4-dimethylaminophenyl)-6-dimethylaminophthalide or, as this compound has been more simply designated, Crystal Violet Lactone (CVL).

The processes of this invention also afford 2-[bis(phenyl)methyl]-5-N-R-N-$R^1$-aminobenzoic acids of the type represented by Formula II. The 2-[bis(phenyl)methyl]-5-N-R-N-$R^1$-aminobenzoic acids of Formula II are primarily useful as intermediates to the phthalides depicted by Formula I. Moreover, the 2-[bis(phenyl)methyl]-5-N-R-N-$R^1$-aminobenzoic acids of Formula II are also useful as color precursors in pressure-sensitive carbonless duplicating systems and in thermal marking systems. They develop color on contact with the acidic clay and phenolic resin developing sheets commonly used in carbonless systems at a much slower rate than do the phthalides of Formula I.

The novel compounds represented by Formulas I and II above are essentially colorless in the depicted form. When the compounds of Formulas I and II are contacted with an acidic medium for example, silica gel or one of the types regularly employed in pressure-sensitive carbonless duplicating systems, for example, silton clay or phenolic resins, they develop a colored image of good to excellent tinctorial strength. The development of color on contact with silica gel, silton clay or a phenolic resin demonstrates that these compounds are highly suitable for use as colorless precursors, that is, color-forming substances in pressure-sensitive carbonless duplicating systems. For such application, the compounds may be incorporated in any of the commercially-accepted systems known in the carbonless duplicating art. A typical technique for such application is as follows. Solutions of the colorless precursor compounds in suitable aromatic solvents are microencapsulated by well-known procedures. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a blue to reddish-purple-colored image of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold.

It has also been found that when the compounds of Formulas I and II are intimately mixed with an acidic developer of the type generally employed in thermal papers, that is, papers which produce a colored image when contacted with a heated stylus or heated type, for example, bisphenol A, heating of the mixture produces a colored image of varying shades from blue to purple depending on the particular compound of the invention employed. The ability of the compounds of Formulas I and II to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

It has been found that the novel process of this invention produces 2-[(Y-phenyl)(4-N-$R^2$-N-$R^3$-aminophenyl)methyl]-5-N-R-N-$R^1$-aminobenzoic acids by interacting a Y-benzaldehyde, an N-$R^2$-N-$R^3$-aniline and a 3-N-R-N-$R^1$-aminobenzoic acid in the presence of an acidic material. This is surprising in view of the well established fact in the art of dyestuff chemistry that a benzaldehyde will react with two equivalents of an aniline, substituted or unsubstituted, to obtain the corresponding triphenyl methane. Furthermore, in view of the known increased reactivity of anilines compared to disubstituted-aminobenzoic acids, which is in keeping with the theory of relative reactivity as taught in basic organic chemistry, it would be expected that the reaction of a mixture consisting of a benzaldehyde, an N-$R^2$-N-$R^3$-aniline and a 3-N-R-N-$R^1$-aminobenzoic acid would result predominantly in a [(Y-phenyl)-bis(N-$R^2$-N-$R^3$-aminophenyl)]methane and a recovery of the 3-N-R-N-$R^1$-aminobenzoic acid. However, it has been found quite unexpectedly that the major product formed by the process of this invention, which comprises interacting a Y-benzaldehyde, an N-$R^2$-N-$R^3$-aniline and a 3-N-R-N-$R^1$-aminobenzoic acid in admixture in the presence of an acidic material, optionally in the presence of urea, is a 2-[(Y-phenyl)(4-N-$R^2$-N-$R^3$-aminophenyl)methyl]-5-N-R-N-$R^1$-aminobenzoic acid with a lesser amount of [(Y-phenyl)-bis(4-N-$R^2$-N-$R^3$-aminophenyl)]methane formed as a by-product.

The process of the instant invention for the preparation of the 3-(Y-phenyl)-3-(4-N-$R^2$-N-$R^3$-aminophenyl)-6-N-R-N-$R^1$-aminophthalides has advantages over the previously known processes for the preparation of these compounds. One advantage of this process is that there are fewer steps involved in the overall synthesis. This contributes to fewer by-products, and also to less solid and liquid waste to be disposed of per unit of desired product. Also with fewer steps involved, the overall synthesis effects an economic production savings per unit of product. Still another advantage over some of the earlier processes is that the instant process obviates the use of heavy metal dioxides, for example, lead dioxide in the oxidation step for conversion of the benzoic acid intermediates to the final phthalide products and in preceeding intermediate steps. Thus the health hazards associated with the use of heavy metals are eliminated by the instant process.

The best mode contemplated by the inventors of carrying out this invention will now be described so as to enable any person skilled in the art to which it pertains to make and use the same.

In accordance with the first of the aforementioned process aspects of this invention, the 3-(Y-phenyl)-3-(4-N-$R^2$-N-$R^3$-aminophenyl)-6-N-R-N-$R^1$-aminophthalides of Formula I are obtained by reacting in the first step approximately equimolar amounts of Y-benzaldehyde, an N-$R^2$-N-$R^3$-aniline and a 3-N-R-N-$R^1$-aminobenzoic acid wherein R, $R^1$, $R^2$, $R^3$ and Y have the same respective meanings given above in Formula I. This reaction is conveniently carried out in an aqueous acidic medium, for example, dilute sulfuric acid, hydrochloric acid or methanesulfonic acid at a temperature in the range of 50° C. to the reflux temperature of the reaction mixture for approximately one hour to approximately thirty hours. The 2-[(Y-phenyl)(4-N-$R^2$-N-$R^3$-aminophenyl)methyl]-5-N-R-N-$R^1$-aminobenzoic acids of Formula II can be isolated by first diluting the reaction mixture with water, secondly adding a sufficient amount of alkali, for example, sodium hydroxide, potassium hydroxide or ammonium hydroxide to render the mixture alkaline to a pH in the range of 10.0 to 14.0, and finally adjusting the pH to 3.0 to 5.0 by the addition of an acid, for example, acetic acid, hydrochloric acid or sulfuric acid. The benzoic acids of Formula II can be isolated by filtration or by decantation of the supernatant liquor. The isolated benzoic acids can be purified by conventional means such as trituration, recrystallization or reslurrying with a suitable organic liquid or by dissolving in a suitable alkali and reprecipitating by adding the alkaline solution to a dilute acid solution. Alternatively, the reaction mixture can be rendered alkaline and employed directly in the oxidation step without isolation of the 2-[(Y-phenyl)(4-N-$R^2$-N-$R^3$-aminophenyl)methyl]-5-N-R-N-$R^1$-aminobenzoic acids.

Although the reaction can be simply carried out in the acidic medium as described above, the addition of urea has been found to provide a distinct advantage over the reaction carried out in the acid medium alone.

It has been found that better results are achieved when urea is present. The urea has the effect of increasing the yield of the desired product and accelerating the reaction time. While it is not necessary to run the reaction in the presence of urea, it does provide the advantages described above.

The 3-(Y-phenyl)-3-(4-N-$R^2$-N-$R^3$-aminophenyl)-6-N-R-N-$R^1$-aminophthalides of Formula I are obtained by oxidizing the appropriate 2-[(Y-phenyl)(4-N-$R^2$-N-$R^3$-aminophenyl)methyl]-5-N-$R^1$-N-$R^2$-aminobenzoic acids of Formula II. The oxidation is conveniently carried out in aqueous alkaline solutions, for example, potassium hydroxide or sodium hydroxide, at a temperature in the range of 10° to 50° C. The oxidizing agent can be a chemical oxidizing agent, for example, potassium persulfate, potassium permaganate or hydrogen peroxide. Alternatively, the oxidizing agent can be molecular oxygen either in the form of gaseous oxygen or air. The 3-(Y-phenyl)-3-(4-N-$R^2$-N-$R^3$-aminophenyl)-6-N-R-N-$R^1$-aminophthalide thus produced is separated by filtration or decantation by conventional means. The isolated phthalide can be purified by conventional means such as trituration, recrystallization or reslurrying with a suitable organic liquid.

The Y-benzaldehydes required as starting materials in the preparation of the phthalides of Formula I and the benzoic acids of Formula II form an old and well-known class of compounds readily obtained by conventional processes well-known in the art. The following list of compounds exemplifies Y-benzaldehydes which are useful in the practice of the processes of this invention: benzaldehyde, 2-methylbenzaldehyde, 2-chlorobenzaldehyde, 2-methoxybenzaldeyde, 3-methoxybenzaldehyde, 4-methoxybenzaldehyde, 2-bromobenzaldehyde, 2-ethoxybenzaldehyde, 3-ethoxybenzaldehyde, 4-ethoxybenzaldehyde, 2-fluorobenzaldehyde, 4-isopropylbenzaldehyde, 4-dimethylaminobenzaldehyde, 4-diethylaminobenzaldehyde, 4-di(n-propyl)aminobenzaldehyde, 4-di(isopropyl)aminobenzaldehyde, 4-di(n-butyl)aminobenzaldehyde, 4-di(sec-butylaminobenzaldehyde, 4-benzylaminobenzaldehyde, 4-dibenzylaminobenzaldehyde, and 4-(N-ethylbenzylamino)benzaldehyde.

The N-$R^2$-N-$R^3$-anilines of required as starting materials in the preparation of the pthalides of Formula I and the benzoic acids of Formula II constitute a well-known class of compounds many of which are commercially available or readily obtained by conventional syntheses well-known in the art. The following list of compounds exemplifies N-$R^2$-N-$R^3$-anilines which are useful in the practice of the processes of this invention: N,N-dimethylaniline, N,N-diethylaniline, N,N-di(n-propyl)aniline, N,N-di(isopropyl)aniline, N,N-di(n-butyl)aniline, N,N-di(sec-butyl)aniline, N,N-di(isobutyl)aniline, N-benzyl-N-ethylaniline, N-ethyl-N-methylaniline, N-benzyl-N-methylaniline, N-benzyl-N-n-propylaniline, N-benzyl-N-sec-butylaniline, N-isopropyl-N-methylaniline, N-n-propyl-N-ethylaniline, N,N-dibenzylaniline, N-phenyl-N-methylaniline, N-(4-methylbenzyl)-N-methylaniline, N-(4-chlorobenzyl)-N-ethylaniline, N-(2,4-dichlorobenzyl)-N-methylaniline, and N-(4-methylphenyl)-N-ethylaniline.

The 3-N-R-N-$R^1$-aminobenzoic acids required as starting materials in the preparation of the phthalides of Formula I and the benzoic acids of Formula II belong to a well-known class of compounds and are generally commercially available or readily obtained by conventional means from readily available starting materials.

The following compounds are exemplary of 3-N-R-N-$R^1$-aminobenzoic acids useful in the processes of this invention: 3-aminobenzoic acid, 3-dimethylaminobenzoic acid, 3-methylaminobenzoic acid, 3-(N-methyl-N-ethylamino)benzoic acid, 3-(N-ethyl-N-butylamino)benzoic acid, 3-diethylaminobenzoic acid, 3-(N-ethylbenzylamino)benzoic acid, 3-dibenzylaminobenzoic acid, 3-ethylaminobenzoic acid, 3-[N-butyl-N-(4-chlorobenzyl)amino]benzoic acid, and 3-[N-methyl-N-(4-methylbenzyl)amino]benzoic acid.

The compounds prepared by the processes of this invention form a part of a large and well known class of compounds and have known melting points. In addition, their infrared and nuclear magnetic resonance spectral data are well established and they are readily identifiable in thin-layer chromatographic analysis (TLC). The molecular structures of the compounds made by the processes of this invention were assigned on the basis of the study of their infrared and nuclear magnetic resonance spectra in conjunction with the spectra of compounds prepared by the art described methods and from the results of TLC analysis.

The following examples will further illustrate the invention without, however, limiting it thereto. All melting points are uncorrected.

EXAMPLE 1

With stirring, a mixture of 15.3 g (0.1 mole) of 97.7 percent 4-dimethylaminobenzaldehyde, 6.0 g (0.1 mole) of urea, 24.1 g (0.1 mole) of 98.8 percent N-ethyl-N-benzylaniline, 18.2 g (0.106 mole) of 96.2 percent 3-dimethylaminobenzoic acid, 76.0 ml of water and 14.6 ml of concentrated sulfuric acid was maintained at a temperature in the range of 90° to 95° C. for approximately four and one-half hours. Slowly, 200.0 ml of tap water was added to the reaction mixture and the resulting mixture was cooled to ambient temperature. A solution of 43.0 g of 90 percent potassium hydroxide dissolved in 200.0 ml of water was added dropwise to the mixture. The resulting milky green mixture was adjusted to pH 11.4 with the addition of a small amount of glacial acetic acid and filtered. No solid was collected. The filtrate was adjusted to pH 4.6 by the gradual addition of glacial acetic acid. The solid which formed was collected by filtration and dried in a vacuum oven at approximately 46° C. The solid melted in the oven but solidified upon cooling to room temperature to obtain 48.0 g of a blue-green-colored solid which melted at 59° to 64° C. A small portion of this solid was dissolved in hot dilute sodium hydroxide. The solution was cooled to ambient temperature and made acid by the gradual addition of glacial acetic acid. The solid which precipitated was collected by filtration, washed with water and dried in vacuo. The resulting pale blue-colored solid melted at 64° to 67° C. The nuclear magnetic resonance spectrum of this solid confirmed that approximately 80 percent of the solid had a chemical structure consistent with the compound 2-[(4-dimethylaminophenyl)(4-N-ethyl-N-benzylaminophenyl)methyl]-5-dimethylaminobenzoic acid (Formula II: Y=4—N(CH$_3$)$_2$; R=$R^1$=CH$_3$; $R^2$=C$_2$H$_5$; $R^3$=CH$_2$C$_6$H$_5$). A significant infrared maximum appeared at 1610 (C=O;s) cm$^{-1}$.

EXAMPLE 2

A mixture of 46.0 ml of water, 49.4 g of 70 percent methanesulfonic acid, 14.9 g (0.1 mole) of 4-dimethylaminobenzaldehyde, 16.5 g (0.1 mole) of 3-dimethylaminobenzoic acid and 12.1 g (0.1 mole) of N,N- dimethylaniline was maintained at reflux temperature with stirring for approximately twenty-four hours. After cooling, the resulting solution was added slowly with stirring to a mixture of 700.0 ml of water and 27.0 ml of 50 percent aqueous sodium hydroxide. The resulting solution having a pH of 12.6 was maintained at 60° C. for approximately one hour. Two grams of diatomaceous earth was added to the solution and the resulting mixture was clarified by filtration. The hot filtrate was added slowly with stirring to a solution of 100.0 ml of water and 10.0 ml of glacial acetic acid. Glacial acetic acid was added slowly to adjust the pH to 4.9 and stirring was continued for approximately fifteen minutes. The solid which formed was collected by filtration, washed with water and dried at approximately 50° C. in vacuo to obtain 21.4 g of 2-[bis(4-dimethylaminophenyl)methyl]-5-dimethylaminobenzoic acid (Formula II: $Y=4-N(CH_3)_2$; $R=R^1=R^2=R^3=CH_3$), a pale green-colored solid which melted over the range of 179° to 184° C. After one recrystallization from toluene, the melting point was 210° to 212° C.

EXAMPLE 3

A mixture of 38.0 ml of water, 17.4 g (0.1 mole) of 85.5 percent 4-dimethylaminobenzaldehyde, 6.0 g (0.1 mole) of urea, 12.6 g (0.1 mole) of N,N-dimethylaniline, 18.2 g (0.11 mole) of 3-dimethylaminobenzoic acid and 14.6 ml (0.273 mole) of concentrated sulfuric acid was maintained at a temperature in the range of 90° to 95° C. for approximately two and one-half hours with stirring. Slowly, 240.0 ml of water was added to the reaction mixture and the resulting mixture was stirred for approximately eight hours. The mixture was filtered to remove the insolubles and the filtrate was added with stirring to a solution of 30.0 ml of concentrated ammonium hydroxide dissolved in 150.0 ml of water. The pH of the resultant mixture was adjusted to 11.0 by gradually adding 21.6 g of 90 percent potassium hydroxide. After stirring approximately one-half hour, the mixture was filtered retaining both the filtercake and the filtrate. The filtrate was adjusted to a pH of approximately 4.8 by slowly adding glacial acetic acid. The solid which formed was collected by filtration, washed with water and dried in vacuo to obtain 4.1 g of 2-[bis(4-dimethylaminophenyl)]methyl-5-dimethylaminobenzoic acid (Formula II: $Y=4-N(CH_3)_2$; $R=R^1=R^2=R^3=CH_3$), a solid.

The filtercake from the alkaline filtration above was extracted by resuspending it in a solution of 500.0 ml of water and 5.5 g of 90 percent potassium hydroxide, maintaining the suspension at approximately 50° C. for approximately thirty minutes and filtering the suspension saving both the filtercake and the filtrate. The filtrate was adjusted to a pH of approximately 4.8 by adding glacial acetic acid. The solid which formed was collected by filtration, washed with water and dried in vacuo to obtain an additional 24.6 g of 2-[bis(4-dimethylaminophenyl)methyl]-5-dimethylaminobenzoic acid. One gram of this product was recrystallized from toluene to obtain a pale yellow solid which melted over the range of 212° to 218° C. The filtercake obtained from the alkaline extraction above was extracted a second time to obtain yet another 1.7 g of the desired product.

EXAMPLE 4

With stirring, a mixture of 15.3 g (0.1 mole) of 97.7 percent 4-dimethylaminobenzaldehyde, 6.0 g (0.1 mole) of urea, 14.9 g (0.1 mole) of N,N-diethylaniline, 18.2 g (0.106 mole) of 3-dimethylaminobenzoic acid, 76.0 ml of water and 14.6 ml of concentrated sulfuric acid was maintained at a temperature in the range of 90° to 95° C. for approximately four hours. Slowly, 200.0 ml of water was added and the resulting mixture was cooled to 30° C. The resulting mixture was clarified by filtration to remove a trace of a dark orange solid. The filtrate was adjusted to pH 10.5 by the dropwise addition of a solution consisting of 43.0 g of 90 percent potassium hydroxide dissolved in 200.0 ml of water resulting in an oily dark green-colored tar-like substance separating in the bottom of the mixture. The supernatant liquid was decanted from the tar-like material saving both the liquid and the tar-like substance. The decant was adjusted to pH 4.7 and a second green tar formed. The supernatant liquid was decanted. Approximately two grams from each portion of the tar-like substances were mixed and dissolved in chloroform. The desired product was isolated from the chloroform solution by column chromatography using a column packed with 40–140 mesh silica gel employing chloroform to elute the first two fractions through the column and acetone to elute the third and fourth fractions through the column. The desired product was isolated from the third fraction by allowing the fraction to evaporate to dryness and then triturating the residue with hexane. The resulting solid was collected by filtration and dried in vacuo to obtain 0.6 g of 2-[(4-diethylaminophenyl)(4-dimethylaminophenyl)methyl]-5-dimethylaminobenzoic acid (Formula II: $Y=4-N(CH_3)_2$; $R=R^1=CH_3$; $R^2=R^3=C_2H_5$), a pale green-gray-colored solid which melted at 78° to 83° C. The nuclear magnetic resonance spectrum was consistent with the assigned structure.

EXAMPLE 5

A mixture of 15.3 g (0.1 mole) of 97.7 percent 4-dimethylaminobenzaldehyde, 6.0 g (0.1 mole) of urea, 21.4 g (0.1 mole) of 98.8 percent N-benzyl-N-ethylaniline, 18.2 g (0.106) of 96.2 percent 3-dimethylaminobenzoic acid, 24.0 ml of concentrated hydrochloric acid and 70.0 ml of water was maintained at a temperature in the range of 90° to 95° C. for approximately four and one-half hours. After cooling to room temperature, a solution of 300.0 ml of water and 43.0 g of 90 percent potassium hydroxide was added dropwise to the reaction mixture. While maintaining a temperature of less than 40° C., there was added gradually 29.1 g (0.1 mole) of 93 percent potassium persulfate. The resultant mixture was stirred for approximately sixteen hours. A blue tar-like material was collected by decanting the supernatant liquid and was dried in a vacuum oven at approximately 66° C. to obtain 49.8 g of blue tar which analyzed by ultraviolet spectroscopy was determined to contain 25.7 g of 3-(4-dimethylaminophenyl)-3-[4-(N-benzyl-N-ethyl)aminophenyl]-6-dimethylaminophthalide (Formula I: $Y=4-N(CH_3)_2$; $R=R^1=CH_3$; $R^2=C_2H_5$; $R^3=CH_2C_6H_5$).

EXAMPLE 6

A. With stirring, a mixture of 15.3 g (0.1 mole) of 97.7 percent 4-dimethylaminobenzaldehyde, 6.0 g (0.1 mole) of urea, 21.4 g (0.1 mole) of 98.8 percent N-ethyl-N-benzylaniline, 18.2 g (0.106 mole) of 96.2 percent 3-dimethylaminobenzoic acid, 76.0 ml of water and 14.6 ml of concentrated sulfuric acid was maintained at a temperature in the range of 90° to 95° C. for approximately four and one-half hours. Slowly, 200.0 ml of water was added to the reaction mixture and the diluted mixture was cooled to approximately 30° C. After clarification by filtration to remove a trace of insolubles, the filtrate was adjusted to pH 11.4 by the gradual addition of a solution consisting of 200.0 ml of water and 43.0 g of 90 percent potassium hydroxide. The pH of the solution was adjusted to 4.6 by gradually adding glacial acetic acid. The solid which formed was collected by filtration and dried in vacuo to obtain 50.8 g of a soft, sticky blue product. The sticky product was dissolved in dilute hydrochloric acid with heating. Gradually the pH was adjusted to 3.5 with the addition of dilute sodium hydroxide. The solid which formed was collected by filtration and washed with water. The filter cake coalesced into a tar-like mass. The tar-like mass was dissolved in a mixture of glacial acetic acid, water and hydrochloric acid. The pH of the solution was adjusted gradually by adding dilute sodium hydroxide while collecting four fractions, one each at pHs of 2.6, 2.9, 3.6 and 4.6 by filtration of the solid which precipitated. Each of the fractions were analyzed by thin layer chromatography. The fractions obtained at pH 3.6 and 4.6 contained predominantly the desired 2-[(4-dimethylaminophenyl)(4-N-ethylbenzylaminophenyl)methyl]-5-dimethylaminobenzoic acid (Formula II: Y=4—N(CH$_3$)$_2$; R=R$^1$=CH$_3$; R$^2$=C$_2$H$_5$; R$^3$=CH$_2$C$_6$H$_5$).

B. The fraction isolated at pH 3.6 was suspended in water and then dissolved by adding dilute sodium hydroxide solution with gentle heating. Gradually, potassium persulfate was added to the solution until no additional precipitate formed. The solid was collected by filtration, ashed with water and dried to obtain predominantly 3-(4-dimethylaminophenyl)-3-[4-(N-ethylbenzylaminophenyl)]-6-dimethylphthalide (Formula I: Y=4—N(CH$_3$)$_2$; R=R$^1$=CH$_3$; R$^2$=C$_2$H$_5$; R$^3$=CH$_2$C$_6$H$_5$), a blue-colored solid. After recrystallization from toluene the blue-gray-colored solid had both an infrared spectrum and a nuclear magnetic resonance spectrum concordant with the assigned structure.

It is contemplated that by following procedures similar to those described in the foregoing examples but interacting the appropriate Y-benzaldehyde, the appropriate 4-N-R$^2$-N-R$^3$-aniline and the appropriate 3-N-R-N-R$^1$-aminobenzoic acid, in the acidic medium shown in Column 5 hereinbelow there will be obtained the 2-[(Y-phenyl)(4-N-R$^2$-N-R$^3$-aminophenyl)methyl]-5-N-R-N-R$^1$-aminobenzoic acids of Formula II described in Column 6 hereinbelow and that said benzoic acids of Column 6 can be oxidized with the oxidizing agents shown in Column 7 hereinbelow to obtain the 3-(Y-phenyl)-3-(4-N-R$^2$-N-R$^3$-aminophenyl)-6-N-R-N-R$^1$-aminophthalides of Formula I, Examples 7–20, presented in Table A hereinbelow.

TABLE A

PART I

| Example No. | Y-Benzaldehyde | N—R$^2$—N—R$^3$—Aniline | 3-N—R—N—R$^1$—Aminobenzoic Acid | Acidic Medium |
|---|---|---|---|---|
| 7 | Benzaldehyde | N,N—Di-n-butylaniline | 3-Diethylaminobenzoic acid | Methanesulfonic acid |
| 8 | 2-Methylbenzaldehyde | N,N—Di-isopropylaniline | 3-N—Ethyl-N—methylaminobenzoic acid | Chloroacetic acid |
| 9 | 2-Chlorobenzaldehyde | N—Benzyl-N—ethylaniline | 3-Di-n-propylaminobenzoic acid | Phosphoric acid |
| 10 | 3-Methoxybenzaldehyde | N,N—sec-Butylaniline | 3-N—Ethylbenzylaminobenzoic acid | Methanesulfonic acid |
| 11 | 4-Methoxybenzaldehyde | N—Ethyl-N—methylaniline | 3-Methylaminobenzoic acid | Acetic acid |
| 12 | 4-Ethoxybenzaldehyde | N,N—Di-n-Propylaniline | 3-Dibenzylaminobenzoic acid | Dichloroacetic acid |
| 13 | 4-Diethylaminobenzaldehyde | N—(4-Chlorobenzyl)-N—methylaniline | 3-Diethylaminobenzoic acid | Trichloroacetic acid |
| 14 | 4-Di-isopropylaminobenzaldehyde | N—n-Propyl-N—benzylaniline | 3-[N—(4-Chlorobenzyl)-N—n-butylamino]-benzoic acid | Acetic acid |
| 15 | 4-Benzylaminobenzaldehyde | N,N—Dibenzylaniline | 3-Di-n-propylaminobenzoic acid | Chloroacetic acid |
| 16 | 4-N—Ethylbenzylaminobenzaldehyde | N—Phenyl-N—methylaniline | 3-Diethylaminobenzoic acid | Methanesulfonic acid |
| 17 | 4-Dibenzylaminobenzaldehyde | N—(4-Methylbenzyl)-N—methylaniline | 3-Aminobenzoic acid | Dichloroacetic acid |
| 18 | 4-Di-sec-butylaminobenzaldehyde | N—(2,4-Dichlorobenzyl)-N—methylaniline | 3-Methylaminobenzoic acid | Trichloroacetic acid |
| 19 | 4-Di-n-propylaminobenzaldehyde | N—(4-Methylphenyl)-N—ethylaniline | 3-Benzylaminobenzoic acid | Phosphoric acid |
| 20 | 4-Isopropylbenzaldehyde | N—Benzyl-N—n-propylaniline | 3-Diethylaminobenzoic acid | Methanesulfonic acid |

PART II

| Example No. | Benzoic Acid of Formula II | Oxidizing Agent | Phthalide of Formula I |
|---|---|---|---|
| 7 | 2-[Phenyl(4-di-n-butylaminophenyl)methyl]-5-diethyl- | Hydrogen peroxide | 3-Phenyl-3-(4-di-n-butylaminophenyl)-6-diethylaminophthalide |

TABLE A-continued

| | Benzoic Acid of Formula V | Oxidizing Agent | Phthalide of Formula I |
|---|---|---|---|
| | aminobenzoic acid | | |
| 8 | 2-[(2-Methylphenyl)(4-di-iso-propylaminophenyl)methyl]-5-(N—ethyl-N—methyl)aminobenzoic acid | Oxygen | 3-(2-Methylphenyl)-3-(4-di-iso-propylaminophenyl)-6-(N—ethyl-N—methyl)aminophthalide |
| 9 | 2-[(2-Chlorophenyl)(4-N—ethylbenzylaminophenyl)methyl]-5-di-n-propylaminobenzoic acid | Potassium permaganate | 3-(2-Chlorophenyl)-3-(4-N—ethylbenzylaminophenyl)-6-di-n-propylaminophthalide |
| 10 | 2-[(3-Methoxyphenyl)(4-di-sec-butylaminophenyl)methyl]-5-(N—ethylbenzylamino)benzoic acid | Air | 3-(3-Methoxyphenyl)-3-(4-di-sec-butylaminophenyl)-6-N—ethylbenzylaminophthalide |
| 11 | 2-[(4-Methoxyphenyl)(4-N—ethyl-N—methylaminophenyl)methyl]-5-methylaminobenzoic acid | Hydrogen peroxide | 3-(4-Methoxyphenyl)-3-(4-N—ethyl-N—methylaminophenyl)-6-methylaminophthalide |
| 12 | 2-[(4-Ethoxyphenyl)(4-di-n-propylaminophenyl)methyl]-5-dibenzylaminobenzoic acid | Oxygen | 3-(4-Ethoxyphenyl)-3-(4-di-n-propylaminophenyl)-6-dibenzylaminophthalide |
| 13 | 2-{(4-Diethylaminophenyl)[(4-N—(4-chlorobenzyl)-N—methylaminophenyl]methyl}-5-diethylaminobenzoic acid | Potassium permaganate | 3-(4-Diethylaminophenyl)-3-[4-N—(4-chlorobenzyl)-N—methylaminophenyl]-6-diethylaminophthalide |

| Example No. | Benzoic Acid of Formula V | Oxidizing Agent | Phthalide of Formula I |
|---|---|---|---|
| 14 | 2-[(4-Di-isopropylaminophenyl)(4-N—propylbenzylamino)methyl]-5-[N-(4-chlorobenzyl)-N—butylamino]benzoic acid | Air | 3-(4-Di-isopropylaminophenyl)-3-(4-N—propylbenzylamino)-6-[N—(4-chlorobenzyl)-N—butylaminophthalide |
| 15 | 2-[(4-Benzylaminophenyl)(4-dibenzylaminophenyl)methyl]-5-di-n-propylaminobenzoic acid | Potassium persulfate | 3-(4-Benzylaminophenyl)-3-(4-dibenzylaminophenyl)-6-di-n-propylaminophthalide |
| 16 | 2-[(4-N—Ethylbenzylaminophenyl)(4-N—methyl-N—phenylamino)methyl]-5-diethylaminobenzoic acid | Hydrogen | 3-(4-N—Ethylbenzylaminophenyl)-3-(4-N—methyl-N—phenylaminonphenyl-6-diethylaminophthalide |
| 17 | 2-{(4-Dibenzylaminophenyl)[4-N—(4-methylbenzyl)-N—methylaminophenyl]methyl}-5-aminobenzoic acid | Oxygen | 3-(4-Dibenzylaminophenyl)-3-[4-N—(4-methylbenzyl)-N—methylaminophenyl]-6-aminophthalide |
| 18 | 2-{(4-Di-sec-butylaminophenyl)[4-N—(2,4-dichlorobenzyl)-N—methylaminophenyl]methyl}-5-methylaminobenzoic acid | Air | 3-(4-Di-sec-butylaminophenyl)-3-[4-N—(2,4-dichlorobenzyl)-N—methylaminophenyl]-6-methylaminophthalide |
| 19 | 2-{(4-Di-n-propylaminophenyl)[4-N—(4-methylphenyl)-N—ethylaminophenyl]methyl}-5-benzylaminobenzoic acid | Hydrogen peroxide | 3-(4-Di-n-propylaminophenyl)-3-[4-N—(4-methylphenyl)-N—ethylaminophenyl]-6-benzylaminophthalide |
| 20 | 2-[(4-Isopropylphenyl)(4-N—n-propylbenzylaminophenyl)methyl]-5-diethylaminobenzoic acid | Potassium persulfate | 3-(4-Isopropylphenyl)-3-(4-N—n-propylbenzylaminophenyl)-6-diethylaminophthalide |

What is claimed is:

1. A process for the production of 2-[(Y-phenyl)(4-N-R²-N-R³-aminophenyl)methyl]-5-N-R-N-R¹-aminobenzoic acids of the formula

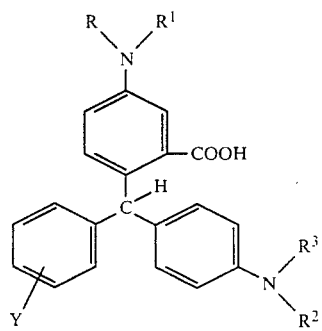

wherein:
R, R¹, R² and R³ may be identical or different and each represents hydrogen, non-tertiary alkyl of one to four carbon atoms, hydroxyalkyl of two or three carbon atoms, phenyl or benzyl or phenyl or benzyl substituted in the benzene ring by one or two of halo or alkyl of one to three carbon atoms; and
Y represents hydrogen, halo, non-tertiary alkyl of one to four carbon atoms, non-tertiary alkoxy of one to four carbon atoms, or dialkylamino or N-alkylbenzylamino in which alkyl is non-tertiary alkyl of one to four carbon atoms and benzyl may be substituted in the benzene ring by one or two of halo or alkyl of one to three carbon atoms which comprises reacting in approximately equimolecular proportions a Y-benzaldehyde, an N-R²-N-R³-aniline and a 3-N-R-N-R¹-aminobenzoic acid in which R, R¹, R², R³ and Y have the meanings given for Formula II, in an acidic medium.

2. A process according to claim 1 for preparing a 2-[(4-Y-phenyl)(4-N-R²-N-R³-aminophenyl)methyl]-5-N-R-N-R¹-aminobenzoic acid.

3. A process according to claim 2 for preparing a 2-[(4-Y-phenyl)(4-N-R²-N-R³-aminophenyl)methyl]-5-N-R-N-R¹-aminobenzoic acid wherein Y is a dialkylamino or N-alkylbenzylamino in which alkyl is a nontertiary alkyl of one to four carbon atoms.

4. A process according to claim 3 for preparing a 2-[(4-Y-phenyl)(4-N-R²-N-R³-aminophenyl)methyl]-5-N-R-N-R¹-aminobenzoic acid wherein R, R¹, R² and R³ are nontertiary alkyl of one to four carbon atoms or benzyl.

5. A process according to claim 1 for preparing a 2-[(4-Y-phenyl)(4-N-R²-N-R³-aminophenyl)methyl]-5-N-R-N-R¹-aminobenzoic acid wherein the acidic medium is selected from the group consisting of aqueous sulfuric acid, hydrochloric acid and methanesulfonic acid.

* * * * *